(12) United States Patent
Vallayer et al.

(10) Patent No.: US 7,452,394 B2
(45) Date of Patent: Nov. 18, 2008

(54) DEVICE FOR COLLECTING AND SEPARATING PARTICLES AND MICROORGANISMS PRESENT IN AMBIENT AIR

(75) Inventors: Bruno Vallayer, Bordeaux (FR); Daniel Trouchet, Paris (FR); Amandine Verdier, Versailles (FR); Emmanuelle Sorel, Beynes (FR)

(73) Assignee: Bertin Technologies (FR)

( * ) Notice: Subject to any disclaimer, the term of this patent is extended or adjusted under 35 U.S.C. 154(b) by 399 days.

(21) Appl. No.: 11/291,724

(22) Filed: Dec. 1, 2005

(65) Prior Publication Data

US 2006/0144025 A1   Jul. 6, 2006

Related U.S. Application Data

(63) Continuation of application No. PCT/FR2004/001382, filed on Jun. 3, 2004.

(30) Foreign Application Priority Data

Jun. 4, 2003  (FR) .................................. 03 06749

(51) Int. Cl.
  *B01D 50/00* (2006.01)

(52) U.S. Cl. ........................... 55/337; 55/459.1; 96/316; 96/413; 73/863.21

(58) Field of Classification Search ................. 55/459.1, 55/337; 96/314, 316, 318, 413; 73/863.21
See application file for complete search history.

(56) References Cited

U.S. PATENT DOCUMENTS

| | | | |
|---|---|---|---|
| 3,070,990 A | * | 1/1963 | Krinov ....................... 73/23.31 |
| 5,500,369 A | | 3/1996 | Kiplinger |
| 5,902,385 A | | 5/1999 | Willeke et al. |
| 6,589,323 B1 | * | 7/2003 | Korin .......................... 96/223 |

FOREIGN PATENT DOCUMENTS

CA    2 151 893 A    12/1996

\* cited by examiner

*Primary Examiner*—Robert A Hopkins
(74) *Attorney, Agent, or Firm*—Alston & Bird LLP

(57) ABSTRACT

A device for collecting particles and microorganisms present in ambient air, the device comprising means for sucking air into a small volume enclosure in which the particles and microorganisms are separated from the sucked-in air by centrifuging, the device being portable, self-contained, and capable of being handled in one hand only, e.g. by means of a handle associated with the air suction means.

17 Claims, 4 Drawing Sheets

DEVICE FOR COLLECTING AND SEPARATING PARTICLES AND MICROORGANISMS PRESENT IN AMBIENT AIR

CROSS-REFERENCE TO RELATED APPLICATIONS

This application is a continuation of PCT/FR2004/001382, filed Jun. 3, 2004, which claims priority from French Priority No. 0306749, filed Jun. 4, 2003.

The invention relates to a device for collecting and separating particles and microorganisms present in ambient air, for the purposes of identifying and counting such particles and microorganisms.

BACKGROUND OF THE INVENTION

Qualitative and quantitative evaluation of particles and microorganisms in air is important in numerous fields such as: the pharmaceutical industry; the agrifood industry; medicine; sanitary services; veterinary services, etc. The dimensions of the particles and microorganisms for collection may lie in the range about 0.5 micrometers ($\mu$m) to about 15 $\mu$m.

The biological particles present in air comprise in particular bacteria, molds, viruses, pollens, etc., and they are generally collected by impact on a nutritive or selective agar-agar culture medium, or by impact on a liquid surface, or indeed by centrifuging in a liquid medium.

The collecting of such particles or microorganisms by impact on agar-agar is followed by incubation, and the colonies that are obtained by culturing are counted and identified. A drawback of that method is that only those microorganisms that are viable and cultivatable on the medium used can be counted, while it is not possible to count microorganisms that are already stressed on being collected or that become stressed as the result of being sucked in or made to impact against agar-agar.

That method can therefore be implemented using only very low air suction flow rates and for short lengths of time in order to avoid damaging the collected microorganisms, and also to avoid drying out the agar-agar, with said air flow rate typically being less than 100 liters per minute (L/min). The microbial load measured with that method is generally under-evaluated.

When collecting by impact on a liquid surface, the particles present in the sucked-in air are projected against wet walls of a chamber and they are recovered at the bottom of the chamber in the form of a liquid sample. a drawback with that method is the bubbling of the liquid caused by the flow of air and the re-dispersion of particles by bouncing against the walls of the chamber.

When collecting by centrifuging in a liquid medium, the particles are sucked into a cylindrical chamber where they are set into rotation and then fall into a tube containing a liquid. The largest particles are pressed against the walls of the chamber and recovered from the bottom, while the finest particles are carried towards the outlet by the air flow and are not collected. In existing systems, the air flow rates used are relatively high in order to ensure that sufficient particles and microorganisms are collected, and the dimensions and the weight of the equipment used (cyclone chamber, air suction means) are relatively large so that the equipment is stationary and installed on a permanent basis, which restricts possible uses thereof.

In addition, the collected particles are generally recovered in a flask at the bottom end of the cylindrical chamber, and the flask is then closed by means of a stopper. That way of proceeding firstly fails to ensure that all of the separated particles are indeed collected in the flask, and secondly does not avoid risks of contamination while the flask is being separated from the cyclone chamber.

OBJECTS AND SUMMARY OF THE INVENTION

An object of the invention is to provide a device for collecting and separating particles and microorganisms present in ambient air, which device combines the advantages of known techniques without presenting the drawbacks.

To this end, the invention provides a method of collecting particles and microorganisms present in ambient air, the device comprising means for sucking air into an enclosure that includes means for retaining particles and microorganisms and means for allowing the sucked-in air to exit, wherein said enclosure is releasably mounted on the device and forms a receptacle for transporting the collected particles and microorganisms.

Thus, in the invention, it is the same element that is used for separating and collecting the particles and microorganisms present in ambient air, and also for transporting them for analysis purposes. This reduces handling and diminishes the risks of the collected particles and microorganisms being contaminated. This also guarantees that the particles and microorganisms that are analyzed represent 100% of the particles and microorganisms that are collected.

According to another characteristic, the enclosure includes means for automatically closing orifices in its top end, these means being open while the enclosure is mounted on the device and being closed while it is separate from the device.

For example, these automatic closure means comprise an annular diaphragm and means for resiliently returning the diaphragm into a position for closing the open top end of the enclosure. When necessary, other means are provided for shutting off one or more orifices for admitting air into the enclosure.

This automatic closing of the enclosure on being separated from the device avoids any risk of the collected particles and microorganisms being contaminated.

The enclosure may be mounted on the device by resilient snap-fastening and by turning through one-fourth of a turn, the movement in translation of the enclosure during its snap-fastening or its one-fourth turn ensuring without difficulty that the above-mentioned automatic closure means are opened or shut.

According to yet another characteristic of the invention, the enclosure essentially comprises a cylindrical chamber of small volume, less than about 200 cubic centimeters ($cm^2$), into which the particles or microorganisms conveyed by the sucked-in air are set into rotation about the axis of the enclosure and are separated from the sucked-in air by centrifuging against the inside wall of the enclosure, said enclosure together with the air-suction means constituting a self-contained assembly that can be carried and manipulated using only one hand.

As an essential advantage, the device of the invention has the ability to be used in any location, because it is self-contained, because of its small volume, and because of its low weight, thus making it possible not only for it to be transported easily, but also for it to be manipulated in one hand only, and for it to be positioned and pointed at will.

This device thus makes it possible to take successive samples from a plurality of locations and to point the device differently from one location to another, for example in the same premises. In particular, the operator may be provided with equipment having a plurality of spare enclosures, thus enabling a plurality of samples to be taken after one another over a short length of time.

Preferably, the removable enclosure is for single use only, or else it is made of a material that can be put into an autoclave.

In a first embodiment of the invention, particles and microorganisms are collected and recovered in the enclosure while dry, and subsequently an appropriate liquid is added in predetermined quantity in said bottom portion in order to obtain a liquid sample that can then be processed in desired manner.

In another embodiment of the invention, the device includes means for injecting liquid into the top portion of the enclosure mounted on the device, said injection means opening out into the means for admitting air into the enclosure, for example.

In this way, a liquid sample is obtained directly in the bottom portion of the enclosure, said sample containing the collected particles and microorganisms.

In a particularly advantageous embodiment, the device of the invention includes a handle that is connected to the main portion of the enclosure support and/or to the air suction means, and that contains a tank of liquid, means for putting the liquid in the tank under pressure, and means for connecting the tank to injection means for injecting the liquid into said enclosure.

Advantageously, these connection means include means for controlling the flow rate of the liquid to the injection means.

Furthermore, the handle includes control means for controlling the air suction means.

In a particular embodiment of the invention, the flow rate of the air sucked into the enclosure by the suction means lies in the range about 200 L/min to 400 L/min.

With such a device, sample-taking can last for a few minutes, thus making it possible to collect the particles and microorganisms that are present in a volume of ambient air that lies in the range 1 cubic meter ($m^3$) to 2 $m^3$.

The device of the invention makes it possible to separate and collect particles and microorganisms having dimensions lying typically in the range about 0.5 µm to about 15 µm. In order to collect finer particles of dimensions smaller than about 1 µm, a suitable filter may be placed in the axial air outlet from the above-mentioned enclosure.

BRIEF DESCRIPTION OF THE DRAWINGS

The invention can be better understood and other characteristics, details, and advantages thereof can appear more clearly on reading the following description made by way of example and with reference to the accompanying drawings, in which.

MORE DETAILED DESCRIPTION

Figure 1:
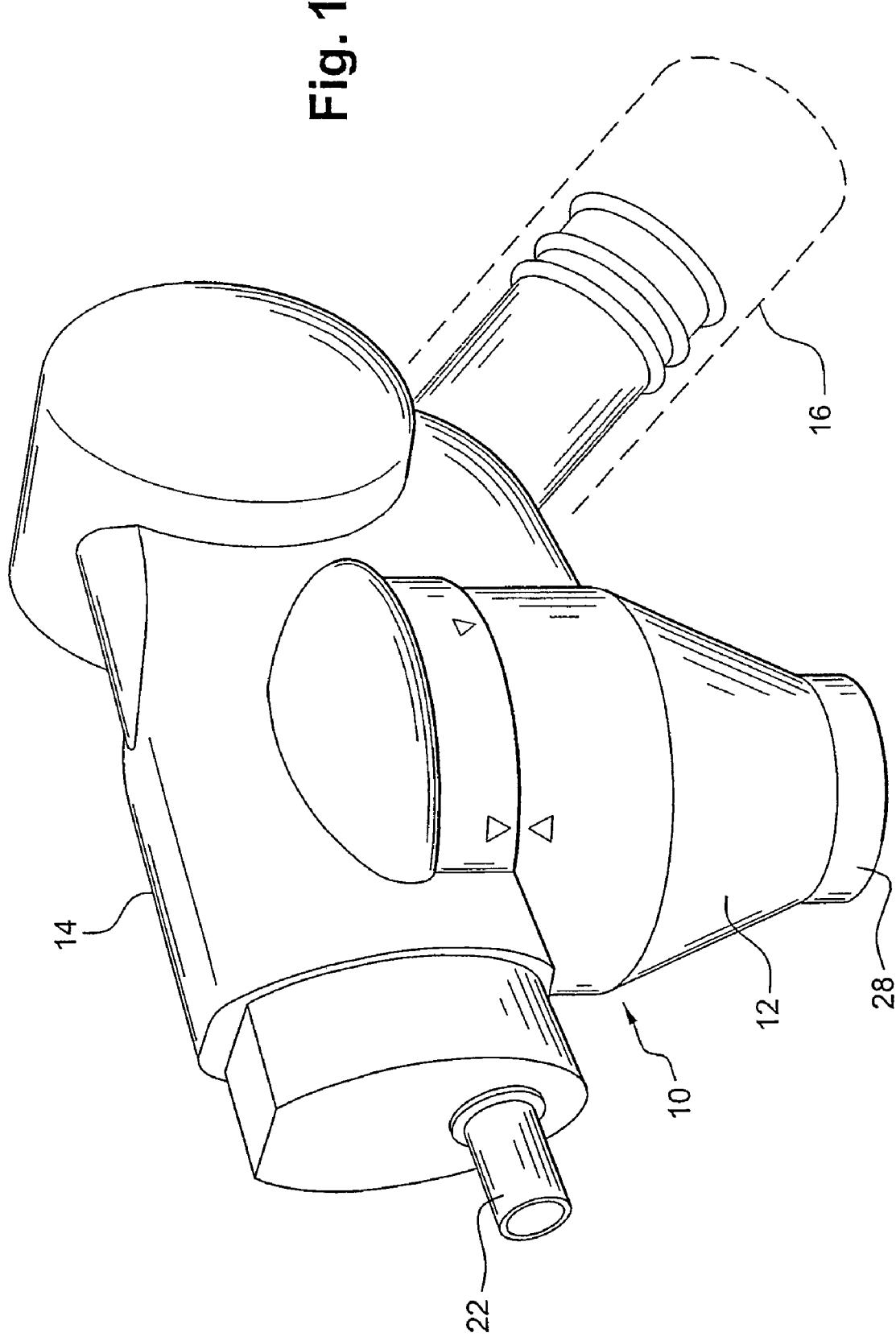
FIG. 1 is diagrammatic perspective view of a first embodiment of a device of the invention.
Figure 2:
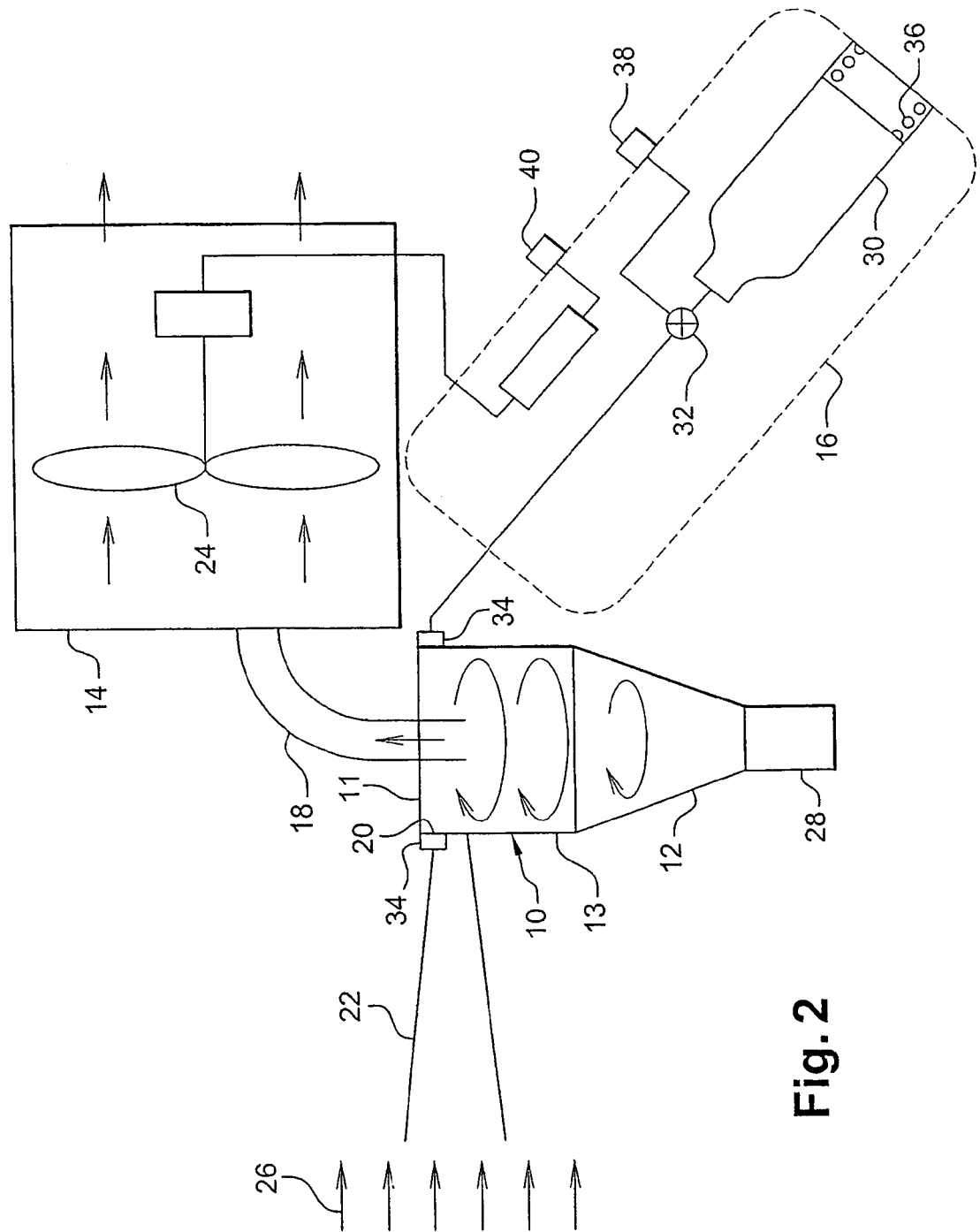
FIG. 2 is a functional diagram of the device.

Reference is made initially to FIGS. 1 to 3 while describing a first embodiment of the device of the invention.

The device is self-contained, portable, and suitable for handling in one hand only, and it essentially comprises a cylindrical enclosure 10 mounted on a main portion of the device and comprising a cylindrical body 13 and a frustoconical bottom portion 12, the enclosure 10 defining a centrifuging chamber and being connected air suction means 14. The device is fitted with a handle 16 provided with means for controlling the operation of the air suction means, these control means being of the pushbutton or slider type, for example.

The main portion of the device on which the enclosure is mounted comprises a top wall 11 with an axial air outlet 18 and a cylindrical rim 20 pointing downwards and including an orifice connected to an air inlet duct 22 that opens out tangentially into the enclosure 10. The wall 11 is secured to the suction means 14 and the axial air outlet 18 is connected to a suction volume formed in the housing of the means 14 and containing a rotor 24 driven by an electric motor and such that rotation thereof regenerates suction in the duct 18, penetration of air into the enclosure 10 via the duct 22, and setting into rotation of the air inside the enclosure as represented by arrows in FIG. 2.

Ambient air 26 is thus sucked into the enclosure 10, and the particles and microorganisms contained therein are separated out by centrifuging and are deposited on the inside wall of the enclosure 10, after which they are recovered in the frustoconical bottom portion 12 of section that tapers downwards and that may include a shutting cylindrical endpiece 28. Advantageously, the cylindrical body 13 and the frustoconical portion 12 of the enclosure form a one-piece unit that is removably mounted on the cylindrical rim 20, by resilient snap-fastening or by turning through one-fourth of a turn.

Figure 3B:
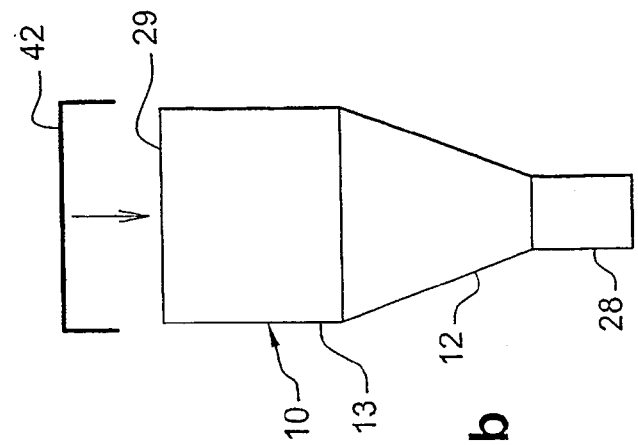
FIGS. 3a and 3b are diagrammatic views showing how the device is used.
Figure 3A:
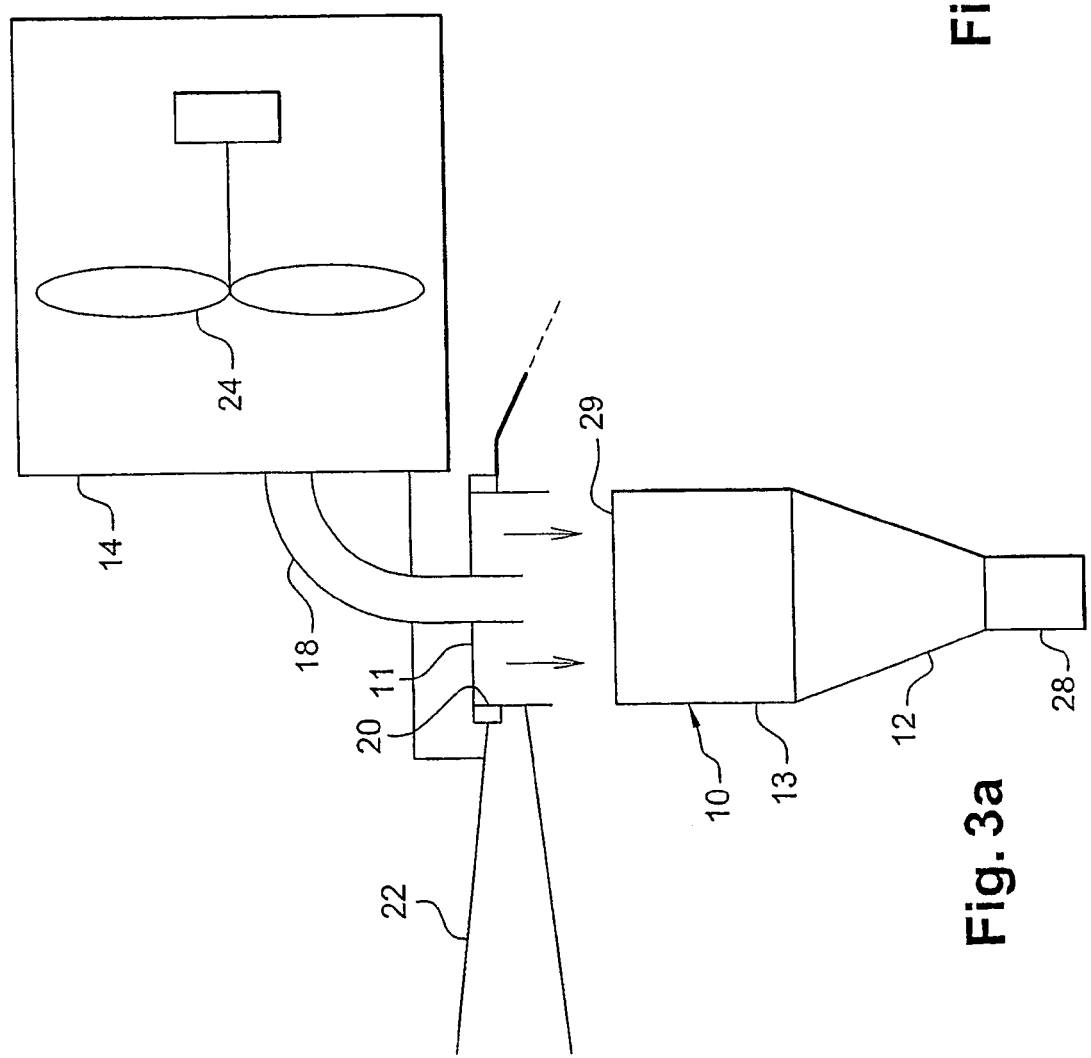

The air inlet orifice and the open top end of the enclosure 10 may be closed by a cap 42 when the enclosure is separated from the device, as shown in FIGS. 3a and 3b, the shut enclosure then forming a receptacle serving to conserve the collected particles and microorganisms and to transport them to a laboratory for analysis.

In a variant, the top end of the enclosure may be fitted with automatic closure means 29, such as an annular diaphragm of the type used in cameras, and associated with a return spring, being actuated to open when the enclosure 10 is mounted on the device and to close when said enclosure is separated from the device.

This automatic shutting of the top end of the enclosure 10 on being separated from the device avoids any risk of external agents contaminating the microorganisms and particles collected in the enclosure 10, or conversely any risk of the external medium being contaminated by the microorganisms and particles collected in the enclosure 10. Appropriate means are provided for closing the orifice for admitting air into the enclosure.

For greater safety, once the top end of the enclosure 10 has been shut by the automatic closure means 29, it can be covered by a cap 42 as shown in FIG. 3b for storage and transport to analyzer means.

In the embodiment shown in FIG. 2, the handle 16 of the device also contains a tank 30 of appropriate liquid (water and a wetting agent, or else some other liquid as a function of the analyses to be performed), with the outlet therefrom including means 32 for adjusting flow rate and connected to means 34 for injection into the top portion of the enclosure 10.

By way of example, the injection means 34 open out into the duct 22 for feeding air into the enclosure.

In a variant, the main top portion of the enclosure includes a plurality of liquid-injection orifices, pointing tangentially and distributed regularly around a circumference of the cylindrical rim 20 and opening out into the enclosure through openings in the top portion of the enclosure 10.

The tank 20 is advantageously associated with means 36 for pressurizing the liquid to be injected, these means 36 being of any suitable type, for example comprising a spring acting on a moving bottom of the tank 30 as shown, a gas under pressure, etc. The tank 30 may itself be a "single-dose" tank, i.e. it may contain a relatively small quantity of liquid that is sufficient for taking one sample, or else it may be a "multiple-dose" tank, in which case it contains a greater quantity of liquid, enabling a plurality of samples to be taken in succession.

The means 32 for controlling the injection flow rate are controlled by a slider or a pushbutton 38 carried by the handle 16, in the vicinity of another pushbutton or slider 40 for controlling the operation of the air suction means 14.

The handle also contains electrical power supply means for powering the electric motor that drives the rotor 24, these means being constituted by rechargeable batteries, or the like, for example. In a variant, the electric motor may be powered by a connection to a power distribution network.

In a particular embodiment of the invention, the enclosure 10 has a diameter of about 50 millimeters (mm), the volume of said enclosure including the bottom portion 12 being about 100 cm$^3$ to 200 cm$^3$, the rate at which air is sucked into the enclosure 10 by the means 14 lying in the range 200 L/min to 400 L/min, the volume of liquid injected into the enclosure 10 by the means 34 each time a sample is taken lying in the range about 5 milliliters (mL) to about 10 mL, the tank 30 containing 40 mL of liquid, for example (thus enabling four to eight samples to be taken), with the installed electrical power being 100 watts (W) to 200 W, and the total weight of the device being less than 2 kilograms (kg).

The device is used as follows.

It can be held in the hand and pointed in a determine direction, or it can be placed on a support. To take a sample, the enclosure 10 is fixed to the cylindrical rim 20 and the air suction means 40 are set into operation using the pushbutton 40. Sample taking may last for 5 minutes (min) for example, thus enabling about 1 m$^3$ to 3 m$^3$ of air to be sucked in, with the sucked-in air flowing through the enclosure 10 while turning about its axis and then rising to leave via the duct 18 and pass through the housing containing the air suction means 14 before being exhausted to the outside. Liquid may be injected continuously throughout the duration of sample taking, or it may be injected during a fraction only of the sample-taking time.

The particles and microorganisms conveyed by the sucked-in air are centrifuged onto the inside wall of the enclosure 10, and are thus separated from the sucked-in air which leaves via the duct 18. The liquid injected into the enclosure 10 circulates, as does the sucked-in air, and serves to wash the entire inside surface of the enclosure. The collected particles and microorganisms are finally recovered in the bottom portion 12 and the cylindrical endpiece 28.

After a sample has been taken, and as shown in FIGS. 3a and 3b, the enclosure 10 can be separated from the top cylindrical rim 20 by unclipping or by turning through one-fourth of a turn, and then the body 13 of the enclosure 10 can be covered by the cap 42 which shuts off all of the orifices in the top portion of the enclosure 10. This provides a small receptacle that is closed in sealed manner and that can be conserved for analysis purposes.

In order to continue taking samples, it then suffices to put another enclosure 10 into place on the top cylindrical rim 20.

The small dimensions of the device of the invention enable it to be transported with a set of four or five removable enclosures in a bag or case, which can also contain one or two spare tanks 30 and possibly also a second rechargeable battery for powering the motor that drives the air suction means 14.

In a variant, the air suction means 14 may include a small tank of compressed air, thus enabling air to be sucked into the cylindrical enclosure 10 by being entrained. The device can then be used without any risk of explosion as might be caused by an electric spark.

In another variant, it is also possible to suck air into the cylindrical enclosure 10 by connecting the device of the invention to a suction socket, of the type that is to be found in certain buildings and hospitals.

In another aspect of the invention, the liquid tank 30 and its pressurizing means 36 can be constituted by an injection syringe that is controlled manually or semi-automatically.

The device of the invention may also used for taking samples and separating particles and microorganisms dry, with the taken and collected particles and microorganisms subsequently being put into solution in a suitable liquid for analysis purposes.

Figure 4:
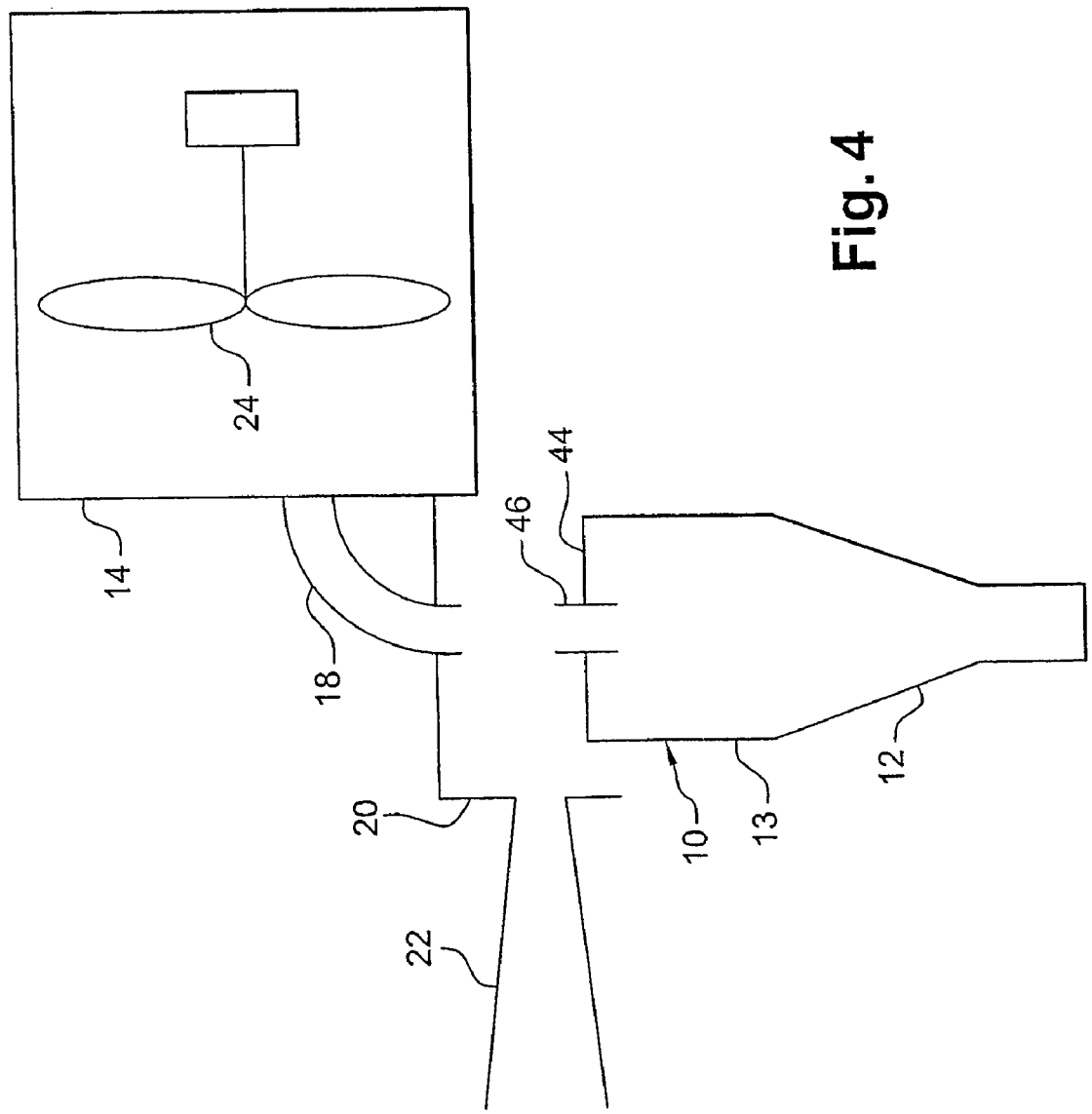
FIG. 4 is a functional diagrammatic view of a variant embodiment of the invention.

One such device is shown diagrammatically in FIG. 4.

With this embodiment, the cylindrical body 13 of the enclosure 10 is closed by a top cover 44 including an axial air outlet 46 optionally fitted with automatic closure means such as a rubber membrane or a sealing gasket, for example. This enclosure 10 is mounted by snap-fastening or by turning through one-fourth of a turn to a main support 20, said support including, as in the preceding embodiment, means 22 for admitting air tangentially into the enclosure 10, an air outlet duct 18 communicating with the volume in which the rotor 24 revolves, and a handle (not shown) enabling the device to be held and manipulated.

After a sample has been taken, the enclosure 10 is separated from the support 20, the orifice for admitting air into the enclosure is closed, and a determined quantity of a suitable liquid can be injected into the enclosure 10 via the top axial duct 46 so as to put into solution the particles and microorganisms that have been deposited on the inside walls of the cylindrical body 13 and of the bottom portion 12 of the enclosure.

In general, the device of the invention makes it possible to recover a representative sample of the particles and microorganisms present in ambient air by taking a volume of ambient air that is relatively large.

The samples that are taken are packaged in the cylindrical enclosures 10 that are separated from the device and they are protected against the risks of contamination. The concentration factor with which the taken particles and microorganisms appear in solution in the injected liquid can be adapted at will. The sampling durations can be adjusted.

The collected samples are separated from one another in the various cylindrical enclosures 10, thus avoiding any risk of contamination between the samples.

In addition, obtaining samples in liquid form makes it possible to apply novel methods of analysis based on the techniques of molecular biology, epifluorescent microscopy, flux cytometry, bioluminescence, immunology, and chromatography. It is thus possible to evaluate the total microbial flora in ambient air and/or the viable microbial flora, without being restricted to evaluating the cultivatable flora, which represents only about 0.1% to about 10% of the total microbial flora.

The novel analysis techniques to which the samples taken by means of the device of the invention can be subjected also make it possible to search specifically for bacteria or molds, or indeed to probe for one species in particular.

Furthermore, the device of the invention together with the above-mentioned bag or case containing accessories such as removable enclosures, one or more tanks of injection liquid, or one more rechargeable batteries, and possibly means for recharging the batteries, etc., constitute a self-contained and portable kit for collecting and separating particles and microorganisms present in ambient air, and capable of finding applications in a very wide variety of very numerous fields.

What is claimed is:

1. A device for collecting and separating particles and microorganisms present in ambient air, the device comprising means for sucking air into a centrifugal enclosure having means for retaining particles or microorganisms and means for exhausting of the sucked-in air, wherein the enclosure is removably mounted on the device and forms a receptacle for transporting collected particles and microorganisms, and wherein the enclosure comprises a small volume cylindrical chamber having volume less than about 200 cm$^3$, in which the particles and microorganisms conveyed by the sucked-in air are set into rotation about the axis of the enclosure and are separated from the sucked-in air by centrifuging against the inside wall of the enclosure, said enclosure co-operating with the air suction means to constitute a self-contained, portable assembly that can be manipulated using only one hand.

2. A device according to claim 1, wherein the means for sucking air into the enclosure is adapted to produce a flow rate of air sucked into said enclosure in the range about 200 L/min to 400 L/min.

3. A device for collecting and separating particles and microorganisms present in ambient air, the device comprising means for sucking air into a centrifugal enclosure having means for retaining particles or microorganisms and means for exhausting of the sucked-in air, wherein the enclosure is removably mounted on the device and forms a receptacle for transporting collected particles and microorganisms, wherein the enclosure includes automatic closure means for closing its top end, which means are open while the enclosure is mounted on the device and are closed while the enclosure is separate from the device.

4. A device according to claim 3, wherein the automatic closure means comprise an annular diaphragm, and resilient means for urging the diaphragm towards its shut position.

5. A device for collecting and separating particles and microorganisms present in ambient air, the device comprising means for sucking air into a centrifugal enclosure having means for retaining particles or microorganisms and means for exhausting of the sucked-in air, wherein the enclosure is removably mounted on the device and forms a receptacle for transporting collected particles and microorganisms, wherein the enclosure is mounted on the device by resilient snap-fastening or by turning through one-fourth of a turn.

6. A device for collecting and separating particles and microorganisms present in ambient air, the device comprising means for sucking air into a centrifugal enclosure having means for retaining particles or microorganisms and means for exhausting of the sucked-in air, wherein the enclosure is removably mounted on the device and forms a receptacle for transporting collected particles and microorganisms, wherein the enclosure is mounted on a main top wall including an axial air outlet and a tangential air inlet.

7. A device according to claim 6, including means for injecting liquid into the top portion of said enclosure, and wherein the liquid injection means comprise a plurality of orifices opening out into said enclosure, that are regularly distributed around a circumference of a rim of the main top wall.

8. A device according to claim 6, wherein said axial outlet of the enclosure is designed to be connected to an air suction socket.

9. A device according to claim 6, wherein the air suction means are secured to the main top wall and suck in air through the axial outlet of the enclosure.

10. A device for collecting and separating particles and microorganisms present in ambient air, the device comprising means for sucking air into a centrifugal enclosure having means for retaining particles or microorganisms and means for exhausting of the sucked-in air, wherein the enclosure is removably mounted on the device and forms a receptacle for transporting collected particles and microorganisms, including means for injecting liquid into the top portion of said enclosure.

11. A device according to claim 10 wherein the means for injecting liquid open out into a duct for admitting air into said enclosure.

12. A device for collecting and separating particles and microorganisms present in ambient air, the device comprising means for sucking air into a centrifugal enclosure having means for retaining particles or microorganisms and means for exhausting of the sucked-in air, wherein the enclosure is removably mounted on the device and forms a receptacle for transporting collected particles and microorganisms, including a handle containing a tank of liquid, means for putting the liquid in the tank under pressure, and means for connecting the tank to means for injecting the liquid into the above-mentioned enclosure.

13. A device according to claim 12, wherein said connection means include means for adjusting the flow rate of liquid towards the injection means.

14. A device according to claim 12, wherein the handle includes control means for controlling the air suction means.

15. A device for collecting and separating particles and microorganisms present in ambient air, the device comprising means for sucking air into a centrifugal enclosure having means for retaining particles or microorganisms and means for exhausting of the sucked-in air, wherein the enclosure is removably mounted on the device and forms a receptacle for transporting collected particles and microorganisms, wherein the removable enclosure is for single use, or is made of a material suitable for putting in an autoclave.

16. A device for collecting and separating particles and microorganisms present in ambient air, the device comprising means for sucking air into a centrifugal enclosure having means for retaining particles or microorganisms and means for exhausting of the sucked-in air, wherein the enclosure is removably mounted on the device and forms a receptacle for transporting collected particles and microorganisms, wherein the means for exhausting air from said enclosure include a filter for capturing particles and microorganisms of dimensions smaller than about 1 µm.

17. A self-contained and portable kit for separating and collecting particles and microorganisms present in ambient air, the kit comprising a device for collecting and separating particles and microorganisms present in ambient air, the device comprising means for sucking air into a centrifugal enclosure having means for retaining particles or microorganisms and means for exhausting of the sucked-in air, wherein the enclosure is removably mounted on the device and forms a receptacle for transporting collected particles and microorganisms, together with a bag of accessories comprising removable spare enclosures; at least one tank of injection liquid; and at least one rechargeable battery.

* * * * *